(12) United States Patent
Bernuetz

(10) Patent No.: US 9,901,065 B2
(45) Date of Patent: Feb. 27, 2018

(54) METHOD FOR PRODUCING A EUPHORBIA INTERSPECIFIC HYBRID PLANT WITH RED BRACTS AND NON-FUNCTIONAL SMALL CYATHIA

(71) Applicant: BONZA BOTANICALS PTY LTD, Yellow Rock NSW (AU)

(72) Inventor: Andrew Bernuetz, Silverdale (AU)

(73) Assignee: BONZA BOTANICALS PTY LTD, Yellow Rock, NSW (AU)

( * ) Notice: Subject to any disclaimer, the term of this patent is extended or adjusted under 35 U.S.C. 154(b) by 722 days.

(21) Appl. No.: 14/200,319

(22) Filed: Mar. 7, 2014

(65) Prior Publication Data

US 2014/0283162 A1    Sep. 18, 2014

Related U.S. Application Data

(60) Provisional application No. 61/803,011, filed on Mar. 18, 2013.

(51) Int. Cl.
*A01H 5/12* (2006.01)
*A01H 1/08* (2006.01)
*A01H 4/00* (2006.01)
*A01H 5/02* (2018.01)

(52) U.S. Cl.
CPC ............. *A01H 5/12* (2013.01); *A01H 1/08* (2013.01); *A01H 4/00* (2013.01); *A01H 5/0244* (2013.01)

(58) Field of Classification Search
None
See application file for complete search history.

(56) References Cited

U.S. PATENT DOCUMENTS

| | | |
|---|---|---|
| PP3,160 P | 5/1972 | Ecke |
| PP4,384 P | 2/1979 | Ecke, Jr. |
| PP7,825 P | 3/1992 | Fruehwirth |
| PP8,259 P | 6/1993 | Jacobsen |
| PP8,773 P | 6/1994 | Fruehwirth |
| PP10,160 P | 12/1997 | Jacobsen |
| PP11,124 P | 11/1999 | Fruehwirth |
| 6,515,200 B1 | 2/2003 | Kobayashi |
| PP15,849 P3 | 7/2005 | Kobayashi |
| PP21,324 P2 | 9/2010 | Bernuetz |
| PP21,325 P2 | 9/2010 | Bernuetz |
| PP21,326 P2 | 9/2010 | Bernuetz |
| PP21,327 P2 | 9/2010 | Bernuetz |
| PP23,296 P2 | 1/2013 | Bernuetz |
| PP24,158 P2 | 1/2014 | Kobayashi |
| 2006/0218679 A1* | 9/2006 | Bernuetz ............... A01H 4/008 800/295 |

FOREIGN PATENT DOCUMENTS

| | | |
|---|---|---|
| AU | 2014201140 | 10/2014 |
| EP | 14160580.8 | 9/2014 |
| JP | 2014-050280 | 3/2014 |

OTHER PUBLICATIONS

Basha et al 2009, Euphytica 168: 197-214.*
Milbocker et al 2069 Canadian Journal of Genetics and Cytology 11: 598-601.*
Allard, R. W., "Principles of Plant Breeding", Second Edition, John Wiley and Sons, 1999.
Bernuetz, A., "Studies on breeding dwarf poinsettias (*Euphorbia pulcherrima* Willd.) and the influence of infective agents", Ph.D. Thesis, University of Sydney, 2001, pp. 243-244, 247-256, 271.
Petit, T. L., and Callaway, D. J., edited by Callaway, D. J. and Callaway, B. M., "Breeding Daylilies", Breeding Ornamental Plants, Chapter 3, Timber Press, Inc., 2000, pp. 54 and 65.
Dole, et. al., "National Poinsettia Trials: New Releases for 2006", *Greenhouse Product News*, Feb. 2006, pp. 22-26.
Ecke, et. al., "The Ecke Poinsettia Manual", Ball Publishing, Batavia, Illinois, 2004.
Embry, J.L. and E. A. Nothnagel, "Leaf Senescence of Postproduction Poinsettias in Low-light Stress", *J. Amer. Soc. Hort. Sci.*, 1994, 119(5): pp. 1006-1013.
Ewart, L.C. and D.E. Walker, "Chromosome Numbers of Poinsettia", *J. Hered.*, 1960, 51(5): pp. 203-208.
Forkmann, G., "Flavonoids as Flower Pigments: The Formation of the Natural Spectrum and its Extension by Genetic Engineering", *Plant Breeding*, 1991, 106: pp. 1-26.
Lee, I., et. al., "Phytoplasma induced free-branching in commercial poinsettia cultivars", *Nature Biotechnology*, 1997, 15: pp. 178-182.
Lee, Y. et. al., "Sequential cell wall transformations in response to the induction of a pedicel abscission event in *Euphorbia pulchernme* (poinsettia)", *The Plant Journal*, 2008, 54: pp. 993-1003.
McCoy, R.E. et. al., "Plant Diseases Associated with Mycoplasma-Like Organisms" The Mycoplasmas, vol. V, Academic Press, Inc., 1989, pp. 545-563.
Murashige, T. and Skoog, F., "A Revised Medium for Rapid Growth and Bio Assays with Tobacco Tissue Cultures", *Physiologia Plantarum*, 1962, 15: pp. 473-497.
Nell, T.A., et. al., "Of Poinsettia—A Review", *Acta Horticulturae*, 1995, 405.
Nell, T.A. and R.T. Leonard, "Protecting poinsettias from postproduction losses", *GrowerTalks*, Jul. 1996, pp. 98-99.
Pickens, K.A. and Z.M. Cheng, "Effects of Colchicine and Oryzalin on Callus and Adventitious Shoot Formation of *Euphorbia puchurrima* 'Winter Rose'", *HortScience*, 2006, 41(7): pp. 1651-1655.
Poehlman, J. M., "Breeding Field Crops", University of Missouri, Holt, Rinehart and Winston, Inc., New York, 1966, 14 pgs.
Rose, J.B., et. al., "Induction of Tetraploids for Breeding Hardy Ornamentals", ISHS *Acta Horticulturae* 560: IV International Symposium on In Vitro Culture and Horticultural Breeding, 2001, pp. 109-112.

(Continued)

*Primary Examiner* — David H Kruse
(74) *Attorney, Agent, or Firm* — Wenderoth, Lind & Ponack, L.L.P.

(57) ABSTRACT

The present invention relates to *Euphorbia* interspecific hybrid plants and methods for making the same. In particular, the invention relates to developing diploid, triploid and tetraploid interspecific hybrid plants derived from crosses between *Euphorbia pulcherrima* and F₁ hybrids of *Euphorbia pulcherrima×Euphorbia cornastra*. In addition to providing the diploid, triploid and tetraploid interspecific hybrid plants and plant parts, the invention provides methods for making triploid interspecific hybrid plants with non-functional small cyathia and methods for making tetraploid interspecific hybrid plants with non-functional small cyathia and red bracts.

12 Claims, No Drawings

(56) References Cited

OTHER PUBLICATIONS

Royal Horticultural Society, "RHS Colour Chart", The Royal Horticultural Society, London, 2001.
Stewart, R.N., "Colchicine-Induced Tetraploids in Carnations and Poinsettias", *Proc. Amer. Soc. Hort. Sci.*, 1951, 57: pp. 408-410.
Stewart, R.N., "Inheritance of Bract Color in Poinsettia", *J. Hered.*, 1960, 51(4): pp. 175-177.
Stewart, R.N. and T. Arisumi, "Genetic and Histogenic Determination of Pink Bract Color in Poinsettia", *J. Hered.*, 1966, 57(6): pp. 217-220.
Takamura, T., et al., "Breeding of the Tetrapolid Yellow-Flowered Cyclamen with "EYE"", ISHS *Acta Horticulturae* 454: III International Symposium on New Floricultural Crops, 1998, pp. 119-126.
Van Tuyl, J. M. and Van Holsteijn, H.C.M., "Lily Breeding Research in the Netherlands", ISHS *Acta Horticulturae* 414: International Symposium on the Genus *Lilium*, 1996, pp. 35-45.
Watts, Leslie, "Flower and Vegetable Plant Breeding", Grower Books, London, 1980, pp. 166 and 168.

\* cited by examiner

METHOD FOR PRODUCING A EUPHORBIA INTERSPECIFIC HYBRID PLANT WITH RED BRACTS AND NON-FUNCTIONAL SMALL CYATHIA

CROSS REFERENCE TO RELATED APPLICATIONS

This application claims the benefit of priority from U.S. provisional patent application Ser. No. 61/803,011, filed on Mar. 18, 2013, which is incorporated herein by reference in its entirety.

BACKGROUND OF THE INVENTION

The present invention relates to methods for producing *Euphorbia pulcherrima×Euphorbia cornastra* interspecific hybrid plants having red bracts and non-functional small cyathia and the plants produced by the method. All publications cited in this application are herein incorporated by reference.

The field of the invention relates to horticulture, plant breeding and plant genetics.

The ornamental plant market is large and diverse and within this market there is an ever present need for new innovative products and improvements to increase customer satisfaction and interest. One popular type of plant sold in this market is the Poinsettia (*Euphorbia pulcherrima*). Poinsettia is well known for its colourful bracts (subtending the flowers), which are produced in a range of colours such as red, white, pink, purple and orange. Red is the most popular colour, accounting for the majority of world-wide sales.

Interspecific hybrids have been produced between *Euphorbia pulcherrima* (2n=28) and *Euphorbia cornastra* (2n=28) as described in: Kobayashi, R. *Euphorbia* interspecific hybrid plant, U.S. Pat. No. 6,515,200, filed Oct. 16, 2000 and Bernuetz, A. Method of producing *Euphorbia* interspecific hybrid plants by cutting and then culturing the hybrid embryos, United States Patent publication number 20060218679, filed Sep. 28, 2006. The plants produced from the methods outlined in the two aforementioned references, herein incorporated in their entirety, have a different appearance and some improved characteristics when compared to *Euphorbia pulcherrima*. For example, hybrid plants of *Euphorbia pulcherrima×Euphorbia cornastra* tend to have higher branching capability and smaller bract size when compared to commercially available poinsettias. Hybrid plants of *Euphorbia pulcherrima×Euphorbia cornastra* always have pink bracts and usually lower post-production performance when compared to the most popular poinsettia cultivars. Commercially available cultivars of *Euphorbia pulcherrima×Euphorbia cornastra* include the PRINCETTIA series (Bonza Botanicals, Pty Ltd, U.S. Plant Patents PP23,296; PP21,327; PP21,326; PP21,325; PP21324) and Dulce Rosa (U.S. Plant Patent PP15,849). Mutation breeding can result in varying shades of pink and the cultivar PRINCETTIA MaxWhite (U.S. Plant Patent PP23,296) has white to very faint pink bracts with a pink vein.

The commercially available *Euphorbia pulcherrima×Euphorbia cornastra* hybrids are almost fully male sterile (fertile anthers may occasionally be produced on some cultivars) and all are female sterile. The fact these plants are so infertile limits the ability to perform further breeding work and improvements.

Although the methods outlined in the previously mentioned references have been useful to develop commercially viable ornamental interspecific hybrid *E. pulcherrima×E. cornastra* plants, it has been impossible to develop an interspecific hybrid *E. pulcherrima×E. cornastra* plant by these methods with (a) non-functional small cyathia and (b) red flower bracts.

SUMMARY OF THE INVENTION

The following embodiments and aspects thereof are described in conjunction with systems, tools, and methods which are meant to be exemplary and not limiting in scope. In various embodiments, one or more of the above-described problems have been reduced or eliminated, while other embodiments are directed to other improvements.

In a first aspect, the invention provides a method for producing a tetraploid (*Euphorbia pulcherrima×Euphorbia cornastra*) plant comprising: (a) providing a diploid (2n=28) *Euphorbia pulcherrima×Euphorbia cornastra* plant which could be a suitable male parent plant, preferably possessing such attributes as dark pink bracts, the production of an occasional anther containing some fertile pollen, reasonable post production performance, resistance to branch breakage, dark green foliage and compact habit; (b) providing vegetative shoot tip cuttings of the plant described in (a) above; (c) applying a root promoting hormone to the base of the vegetative shoot tip cuttings; (d) propagating the vegetative shoot tip cuttings to produce rooted cuttings; (e) treating the rooted cuttings with a chemical composition such as colchicine that results in a doubling of the chromosome number of the plant to tetraploid (2n=56); (f) growing the selected chromosome doubled shoots into flowering plants; (g) assessing the pollen production and pollen viability of the resultant putative tetraploid $F_1$ hybrid plant; (h) ascertaining the chromosome number of the plant through cytological analysis and (i) stabilising the plant through successive generations of vegetative propagation.

It is a further aspect of the present invention to provide a tetraploid (*Euphorbia pulcherrima×Euphorbia cornastra*) interspecific hybrid plant with 2n=56 chromosomes.

It is a further aspect of the present invention to provide a plant part of a tetraploid (*Euphorbia pulcherrima×Euphorbia cornastra*) interspecific hybrid plant.

It is a further aspect of the present invention to provide a method of chromosome doubling using colchicine to produce a tetraploid (*Euphorbia pulcherrima×Euphorbia cornastra*) interspecific hybrid plant or part thereof which is clonally propagated.

In a second aspect, the invention provides a method to produce tetraploid *Euphorbia pulcherrima* plants comprising: (a) providing a diploid *Euphorbia pulcherrima* plant (2n=28) which could be a suitable female parent plant, preferably possessing such attributes as dark red bracts, male and female fertility, good post production performance, resistance to branch breakage, dark green foliage and compact habit; (b) providing vegetative shoot tip cuttings of the plant described in (a) above; (c) applying a root promoting hormone to the base of the vegetative shoot tip cuttings; (d) propagating the vegetative shoot tip cuttings to produce rooted cuttings; (e) treating the rooted cuttings with a chemical composition such as colchicine that results in a doubling of the chromosome number of the plant to tetraploid (2n=56); (f) growing the selected chromosome doubled shoots into flowering plants; (g) assessing the female and male fertility of the resultant putative tetraploid $F_1$ hybrid plant; (h) ascertaining the chromosome number of the plant through cytological analysis and (i) stabilising the plant through successive generations of vegetative propagation.

It is a further aspect of the present invention to provide a tetraploid *Euphorbia pulcherrima* plant with 2n=56 chromosomes.

It is a further aspect of the present invention to provide a plant part of a tetraploid *Euphorbia pulcherrima* plant.

It is a further aspect of the present invention to provide a method of chromosome doubling using colchicine to produce a tetraploid *Euphorbia pulcherrima* plant or part thereof which is clonally propagated.

In a third aspect, the invention provides a method to produce backcross triploid interspecific hybrid plants with non-functional small cyathia by crossing a diploid *Euphorbia pulcherrima* plant as a female parent with a tetraploid (*Euphorbia pulcherrima*×*Euphorbia cornastra*) plant as a male parent comprising: (a) cultivating first and second plants where the first plant is a diploid *Euphorbia pulcherrima* plant and the second plant is a tetraploid (*Euphorbia pulcherrima*×*Euphorbia cornastra*) plant; (b) the first plant preferably possesses such attributes as dark red bracts, male and female fertility, good post production performance, resistance to branch breakage, dark green foliage and compact habit; (c) collecting viable pollen from the second plant and applying it to the receptive stigma of the first plant; (d) isolating and cultivating a resultant embryo on suitable media in-vitro and (e) obtaining a triploid 2n=42 chromosome (*Euphorbia pulcherrima*×*Euphorbia cornastra*) interspecific hybrid plant resulting from the growth of this embryo.

It is a further aspect of the present invention to select the final plants for commercial utility based on non-functional small cyathia and other desirable commercial attributes.

A plant part of the backcross triploid (*Euphorbia pulcherrima*×*Euphorbia cornastra*) interspecific hybrid plant is a flower, cutting, seed, pollen, ovule, or cell. A plant is then clonally propagated from the plant part.

It is a further aspect of the present invention that the backcross triploid *Euphorbia pulcherrima*×*Euphorbia cornastra* plant of the present invention has a chromosome number of 2n=42.

It is a further aspect of the present invention that the backcross triploid *Euphorbia pulcherrima*×*Euphorbia cornastra* plant of the present invention is infected with Poinsettia Branch Inducing Phytoplasma (PoiBI).

In a fourth aspect, the invention provides a method to produce tetraploid interspecific hybrid plants with non-functional small cyathia and red bracts by backcrossing a tetraploid *Euphorbia pulcherrima* plant as a female parent with a tetraploid (*Euphorbia pulcherrima*×*Euphorbia cornastra*) plant as a male parent comprising: (a) cultivating first and second plants where the first plant is a tetraploid *Euphorbia pulcherrima* plant and the second plant is a tetraploid (*Euphorbia pulcherrima*×*Euphorbia cornastra*) plant; (b) the first plant preferably possesses such attributes as dark red bracts, male and female fertility, good post production performance, resistance to branch breakage, dark green foliage and compact habit; (c) collecting viable pollen from the second plant and applying it to the receptive stigma of the first plant; (d) isolating and cultivating a resultant embryo on suitable media in-vitro and (e) obtaining a tetraploid 2n=56 chromosome (*Euphorbia pulcherrima*×*Euphorbia cornastra*) backcross plant resulting from the growth of this embryo.

It is a further aspect of the present invention to select the final plants for commercial utility based on non-functional small cyathia, red bracts and other desirable commercial attributes.

A plant part of the backcross tetraploid (*Euphorbia pulcherrima*×*Euphorbia cornastra*) interspecific hybrid plant is a flower, cutting, seed, pollen, ovule, or cell. A plant is then clonally propagated from the plant part.

It is a further aspect of the present invention that the backcross tetraploid *Euphorbia pulcherrima*×*Euphorbia cornastra* plant of the present invention has a chromosome number of 2n=56.

It is a further aspect of the present invention that the backcross tetraploid *Euphorbia pulcherrima*×*Euphorbia cornastra* plant of the present invention is infected with Poinsettia Branch Inducing Phytoplasma (PoiBI).

It is a further aspect of the present invention to provide a method for producing backcross triploid and backcross tetraploid (*Euphorbia pulcherrima*×*Euphorbia cornastra*) plants developed from the third and fourth aspects comprising the steps of: (a) obtaining a cutting of a backcross triploid or backcross tetraploid (*Euphorbia pulcherrima*×*Euphorbia cornastra*) plant, wherein said plant is produced from the cross of a diploid or tetraploid *Euphorbia pulcherrima* female parent and a tetraploid (*Euphorbia pulcherrima*×*Euphorbia cornastra*) plant; and (b) cultivating this cutting to obtain a backcross triploid or backcross tetraploid (*Euphorbia pulcherrima*×*Euphorbia cornastra*) plant.

It is a further aspect of the present invention to provide a method for producing a backcross triploid or backcross tetraploid (*Euphorbia pulcherrima*×*Euphorbia cornastra*) plant further defined by applying a plant hormone composition to the cutting base to induce the formation of roots to produce a plant.

It is a further aspect of the present invention to provide a method for altering the chromosome number of a *Euphorbia pulcherrima* or *Euphorbia pulcherrima*×*Euphorbia cornastra* plant to increase the somatic chromosome number from diploid 2n=2x=28 to tetraploid 2n=4x=56 comprising the steps of: (a) cultivating the plant; (b) applying an antimitotic agent to the growing points of said plant; (c) forcing shoots to emerge from the treated growing points; (d) selecting putative tetraploid shoots thus developed; (e) assessing the chromosome complement of said shoots through cytological karyotype analysis; (f) growing said shoot into a plant; and (g) checking chromosomal stability.

In addition to the exemplary aspects and embodiments described above, further aspects and embodiments will become apparent by study of the following descriptions.

DETAILED DESCRIPTION OF THE INVENTION

In the description and tables that follow, a number of terms are used. In order to provide a clear and consistent understanding of the specification and claims, including the scope to be given such terms, the following definitions are provided:

Abscission. In relation to cyathia it includes the development of an abscission layer followed by aborting of the associated appendage.

Allele. The allele is any of one or more alternative form of a gene, all of which relate to one trait or characteristic. In a diploid cell or organism, the two alleles of a given gene occupy corresponding loci on a pair of homologous chromosomes.

Amiprophos-methyl (APM). As used herein, amiprophos-methyl (APM) refers to a compound used in plant breeding to induce chromosome doubling.

Androecium. Male parts of a plant flower which are collectively termed the stamens.

Allotetraploid. As used herein, allotetraploid means a plant that is diploid for two genomes, each from a different species. For example, allotetraploid *Euphorbia pulcherrima*×*Euphorbia cornastra* plants of the present invention have 2n=56 chromosomes.

Allotriploid. As used herein, allotriploid means a triploid plant having three times the monoploid chromosome number. For example, allotriploid plants of the present invention have 2n=42 chromosomes.

Aneu-tetraploid. As used herein, aneu-tetraploid means a tetraploid plant and any plant having more or less than four times the monoploid chromosome number. For example, aneu-tetraploid *Euphorbia* plants of the present invention have 2n=56+/−several chromosomes.

Aneu-triploid. As used herein, aneu-triploid means a triploid plant and any plant having more or less than three times the monoploid chromosome number. For example, aneu-triploid plants of the present invention have 2n=42+/−several chromosomes.

Anti-mitotic agent. As used herein, anti-mitotic refers to a compound or chemical that is used to block cell growth by stopping mitosis (cell division) used in plant breeding to induce chromosome doubling. Examples of anti-mitotic agents include, but are not limited to, colchicine, trifluralin, oryzalin, and amiprophos-methyl (APM).

Asexual propagation/Asexual reproduction. Asexual propagation or asexual reproduction means every type of plant propagation except for sexually produced seeds. Examples of asexual propagation include, but are not limited to, cuttings, grafting, division, apomixis, or regeneration in tissue culture.

Backcrossing. Backcrossing is a process in which a breeder repeatedly crosses hybrid progeny back to one of the parents, for example, a first generation hybrid $F_1$ with one of the parental genotype of the $F_1$ hybrid.

Bract. A modified leaf structure often coloured, subtending the cyathium in some species of *Euphorbia*.

Cell. As used herein, cell includes a plant cell, whether isolated, in tissue culture, or incorporated in a plant or plant part.

Chimera. A chimera or a chimeric plant is a plant that consists of two or more genetically distinct groups of cells. The genetic distinctness usually originates from a mutation.

Chromosome number. The number of chromosomes possessed by a plant cell.

Chromosomal stability. As used herein, chromosomal stability refers to a chromosome that is not subject to sudden or extreme change or fluctuation.

Colchicine. Colchicine is a pale-yellow alkaloid, $C_{22}H_{25}NO_6$, obtained from the autumn crocus and used in plant breeding to induce chromosome doubling.

Crossing. The pollination of a female flower of a plant, thereby potentially resulting in the production of seed from the flower.

Cross-pollination. Fertilization by the union of two gametes from different plants.

Cutting. A part originating from a plant, such as a stem, leaf, or root, removed from a plant to propagate a new plant, as through rooting or grafting.

Cyathia diameter. The diameter in millimeters, of a primary or secondary cyathium, measured transversely at the widest part of the cyathium.

Cyathium. (Plural: cyathia) is one of the specialized pseudanthia ("false flowers") forming the inflorescence of plants in the genus *Euphorbia* (family Euphorbiaceae). As cyathia are produced on the plant they are described as primary ($1^{st}$), secondary ($2^{nd}$), tertiary ($3^{rd}$), etc.

Diploid. A diploid (denoted by the somatic cell chromosome number 2n=2x) is a somatic cell or plant having one pair of each type of chromosome (homologous pair), so that the basic (monoploid) chromosome number (denoted by the symbol x) is doubled. In the context of this document diploid means 2n=28.

Dominant inheritance. Refers to a mode of inheritance in which the phenotype of a certain characteristic or trait is determined by a dominant allele.

Dominant mutation. The phenotype of a dominant mutation is visible in a heterozygous genotype.

Emasculate. The removal of plant male sex organs or the inactivation of the organs with a chemical agent or a cytoplasmic or nuclear genetic factor conferring male sterility.

Embryo. The young plant individual after fertilization or parthenogenesis when the proembryo has differentiated into embryo and suspensor.

Embryo culture. The growth of isolated plant embryos on suitable media in vitro.

Embryo rescue. As used herein, embryo rescue is the process plant breeders use to attempt to germinate embryos that may be weak, immature, or would otherwise not develop into a mature viable seed on the parent plant. For example, one form of embryo rescue is ovule culture, which involves aseptically removing the ovule from the seed and placing the ovule onto artificial media to enable the embryo to germinate and grow into a plant.

*Euphorbia cornastra*. A plant species from the Euphorbiaceae family which has been partially domesticated, but not commercialized. In the context of this document, unless otherwise stated, the chromosome number of *Euphorbia cornastra* is diploid 2n=28.

*Euphorbia pulcherrima*. A plant species from the Euphorbiaceae family which has been domesticated and is used in commercial horticulture as an ornamental plant. In the context of this document, unless otherwise stated, the chromosome number of *Euphorbia pulcherrima* is diploid 2n=28.

*Euphorbia pulcherrima*×*Euphorbia cornastra*. An interspecific hybrid between diploid *Euphorbia pulcherrima* as a female parent and diploid *Euphorbia cornastra* as a male parent. The resulting chromosome number of the $F_1$ interspecific hybrid is diploid 2n=28.

$F_2$. The "$F_2$" symbol denotes the offspring resulting from the selfing or self mating of members of the first generation, the $F_1$ generation.

Fuzzy cyathia. Cyathia which possesses the characteristic of enlarged internal features which expand outward and force the cyathium open and give it a wooly or fuzzy appearance. Fuzzy cyathia are usually greatly enlarged compared to normal cyathia and are not considered to be a commercially desirable feature of the plant.

Gamete. A cell or nucleus that may participate in sexual fusion to form a zygote.

Gene. As used herein, gene refers to a segment of nucleic acid. A gene can be introduced into a genome of a species, whether from a different species or from the same species, using transformation or various breeding methods.

Genotype. Refers to the genetic constitution of a cell or organism.

Gynoecium. The ovule producing parts of a plant's flower.

Haploid. A haploid is a cell nucleus containing only one representative of each chromosome of the chromosome complement, denoted by the symbol n. The haploid number (n) is the number of chromosomes in a haploid cell nucleus. Gametes are haploid cells.

Heterozygous. Refers to a genetic constitution in which the corresponding alleles of a certain gene locus are different.

Homozygous. Refers to a genetic constitution in which the corresponding alleles of a certain gene locus are identical.

Inbreeding. Is defined as the production of offspring by the fusion of genetically closely related gametes.

Inflorescence. A group or cluster of flowers arranged on a stem that is composed of a main branch or an arrangement of branches.

Interspecific cross. Interspecific cross means the sexual hybridization of two individuals, each from different species of the same genus. For example, a *Euphorbia pulcherrima* plant crossed with a *Euphorbia cornastra* plant.

Interspecific hybrid. Interspecific hybrid means a plant of the $F_1$ generation resulting from an interspecific cross or a cross between two different species.

Karyotype analysis. As used here, karotype analysis means the ascertainment of chromosome number and constitution by light microscopy analysis of stained metaphase chromosomes. Cells are collected, induced to divide, and then arrested at metaphase (a stage of cell division when the chromosome are condensed and therefore visible). The chromsomes are stained with certain dyes that show a pattern of light and dark bands. Large changes in chromosomes can be detected using karyotype analysis.

Locus. A locus confers one or more traits such as, for example, herbicide tolerance, insect resistance, disease resistance, flower color, flower shape, plant height, etc. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

$M_0$. The $M_0$ generation is the generation treated with a mutagen. Subsequent generations are designated $M_1$, $M_2$, $M_3$, etc.

Monoploid. The monoploid chromosome number is the number of chromosomes in a single (non-homologous) set (x) and can be different from the haploid (n) number.

Mutation. Mutations are changes in the DNA sequence of a cell's genome and are caused by mutagens, like radiation or chemicals, as well as by errors that occur spontaneously during DNA replication.

Non-functional small cyathia. The phrase "non-functional small cyathia" describes cyathia with an average diameter measured transversely, of 3 mm or less, which have no sexual capacity because they are lacking functional androecium and gynoecium.

Oryzalin. As used herein, oryzalin refers to a compound used in plant breeding to induce chromosome doubling.

Outbreeding. Also known as outcrossing, is described as the production of offspring by the fusion of distantly related gametes. Outbreeding is the opposite of inbreeding.

Ovule culture. The culture of excised ovules on suitable media in vitro.

Phenotype. Refers to any observable characteristic or trait of a plant, such as flower color, plant size, etc.

Plant. As used herein, the term plant includes reference to an immature or mature whole plant, including a plant from which seed or anthers have been removed. Seed or embryo that will produce the plant is also considered to be the plant.

Plant cell. Plant cell, as used herein includes plant cells whether isolated, in tissue culture, or incorporated in a plant or plant part.

Plant habit. This is a visual assessment of the overall growth phenotype of the plant.

Plant hormone composition. As used herein, a plant hormone composition refers to a chemical that regulates plant growth. For example, Indole-3-butyric acid, $N^6$-benzyl adenine, and gibberellic acid.

Plant part. As used herein, the term "plant part" includes protoplasts, leaves, stems, roots, root tips, anthers, pistils, seed, embryo, pollen, ovules, cotyledon, hypocotyl, cyathium, bract, shoot, tissue, petiole, cells and meristematic cells, and the like.

PoiBI. The abbreviation for Poinsettia Branch Inducing Phytoplasma, which is a phytoplasma that infects certain species of *Euphorbia* and has the effect of increasing the branching of infected plants.

Pollination. Pollination is the process by which pollen is transferred in plants, thereby enabling fertilization and sexual reproduction.

Polyploid. An individual plant carrying more than two complete sets of homologous chromosomes.

Post-production. Post-production means the time after leaving the greenhouse production facility.

Post-production performance. Post-production performance relates to plant quality and the subsequent deterioration in quality from the time it leaves the greenhouse production facility.

Progeny. As used herein, progeny includes an $F_1$ plant produced from the cross of a *Euphorbia pulcherrima* plant with a plant from the pedigree *Euphorbia pulcherrima*× *Euphorbia cornastra*. Progeny further includes, but is not limited to, subsequent $F_2$, $F_3$, $F_4$, $F_5$, $F_6$, $F_7$, $F_8$, $F_9$, and $F_{10}$ generational crosses with the parents and between the progeny.

Recessive inheritance. Refers to a mode of inheritance in which the phenotype of a certain characteristic or trait is determined by a recessive allele.

Recessive mutation. The phenotype of a recessive mutation is visible only in a homozygous genotype.

Regeneration. Regeneration refers to the development of a plant from tissue culture.

Sexual propagation/Sexual reproduction. Refers to the propagation of plants from seeds.

Somatic cell. Any cell of a plant other than the spores, gametes, or their precursors.

Tetraploid. As used herein, tetraploid refers to a cell or plant having a chromosome number that is four times the monoploid number of chromosomes and is designated in somatic cells by $2n=4x$. In the context of this document tetraploid means $2n=56$.

Trifluralin. As used herein, trifluralin refers to a compound used in plant breeding to induce chromosome doubling.

Triploid. As used herein, a triploid refers to a cell or plant having a chromosome number that is three times the monoploid number of chromosomes and is designated in somatic cells by $2n=3x$. In the context of this document triploid means $2n=42$.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants).

Development of Tetraploid (*Euphorbia pulcherrima*×*Euphorbia cornastra*) Hybrid Plants The present invention provides a method for generating tetraploid (*Euphorbia pulcherrima*×*Euphorbia cornastra*) plants defined herein as having a chromosome number of 2n=56. Tetraploid (*Euphorbia pulcherrima*×*Euphorbia cornastra*) plants have not been reported in the available prior art, although in: Bernuetz, A., *Studies on breeding dwarf poinsettias (Euphorbia pulcherrima Willd) and the influence of infective agents*, PhD Thesis, University of Sydney (2001), the author alludes to their potential development and use (pp 243-244, pg 271).

A tetraploid form of *Euphorbia pulcherrima*×*Euphorbia cornastra* plants is developed, preferably by use of an anti-mitotic agent. Examples of anti-mitotic agents include, but are not limited to, colchicine, trifluralin, oryzalin, amiprophos-methyl, and other polyploidy inducing agent(s). Tetraploids can occur spontaneously in nature or be induced using spindle fiber inhibitors, such as colchicine. The technique of colchicine-induced polyploidization has been used since the 1930's. Colchicine inhibits the assembly of tubulin subunits into spindle fibers, such that no chromosome movement can occur and hence, cells at the metaphase stage of mitosis accumulate. When the chromatids separate, but are not divided into separate cells by the spindle, the chromosome number is doubled creating an autopolyploid. When creating a polyploid for breeding purposes, the layer of the apical meristem that gives rise to the gametophytic tissue needs to be doubled. To optimize the probability of successful doubling, a high number of small, actively growing meristems are treated. Usually colchicine is used at a concentration of 0.1% to 2.0% depending on the tissue and the species. Methods for treating seeds with colchicine or other spindle fiber inhibitors are well-known in the art, as discussed in Poehlman, J. M., *Breeding Field Crops*, University of Missouri, Holt, Rinehart and Winston Inc. (1966); Watts, L., *Flower and Vegetable Plant Breeding*, Grower Books (1980); Callaway D. J. and Callaway M. B., *Breeding Ornamental Plants*, Timber Press Inc. (2000).

Ploidy changes affect crossability, fertility, cell size, and heterozygosity. These factors offer potential benefits as well as limitations in plant breeding. Ploidy manipulation was used for the introgression of germplasm between taxa of different ploidy. For example, to overcome $F_1$ sterility of interspecific *Lilium* hybrids, colchicine was used for the induction of tetraploids. Interspecific crosses at the tetraploid level between complex hybrids of four *Lilium* species were made. See, Van Tuyl, J. and van Holsteijn, H. *Lily breeding research in the Netherlands* Acta Horticulturae, 414: 35-45 (1996). Tetraploid plants of *Buddleja globosa*, which is naturally diploid, were produced using colchicine treatment and have been crossed with natural tetraploid *Buddleja davidii* to introduce yellow flower color into *Buddleja davidii*. See, Rose, J., Kubba, J. and Tobutt, K. *Induction of tetraploids for breeding hardy ornamentals*, Acta Horticulturae, 560: 109-112 (2001). All yellow-flowered *Cyclamen persicum* cultivars are diploid and do not have "eyes" on the petals. Using colchicine treatment, a tetraploid yellow-flowered cyclamen was induced. After crossing with tetraploid "eyed" cultivars, segregation was such that yellow-flowered "eyed" selections could not be maintained by seed. See, Takamura, T., Sugimura, T., Tanaka, M. and Kage, T. *Breeding of the yellow flowered tetraploid cyclamen with "eye"*, Acta Horticulturae, 454: 119-126 (1998).

The present invention provides a method of altering the chromosome number of a *Euphorbia pulcherrima*×*Euphorbia cornastra* plant to develop a tetraploid plant, with a chromosome number of 2n=56 comprising the steps of: (a) cultivating the *Euphorbia pulcherrima*×*Euphorbia cornastra* plant; (b) applying an anti-mitotic agent to the growing points of the plant; (c) forcing shoots to emerge from the treated growing points of the plant; (d) selecting putative tetraploid shoots thus developed from the plant; (e) assessing the chromosome complement of the tetraploid shoots through cytological karyotype analysis; (f) growing the tetraploid shoot into a plant; and (g) checking chromosomal stability. It can be appreciated by one skilled in the art that the induction of tetraploidy can result in plants with chromosome numbers higher or lower than the expected tetraploid number and such aneuploid plants are herein defined as aneu-tetraploid.

Development of Tetraploid *Euphorbia pulcherrima* Plants

The present invention provides a method for generating tetraploid *Euphorbia pulcherrima* plants defined herein as having a chromosome number of 2n=56.

In Poinsettia, tetraploid plants have been reported, some as naturally occurring mutations and others induced through the use of colchicine (Bernuetz, A. pp 247-256 (2001); Ewart, L. C. and Walker, D. E., *Chromosome numbers in poinsettia*, The Journal of Heredity 51: 203-207 (1960); Jacobsen, P., Poinsettia Plant "Pearl", United States Plant Patent 10,160 (1997); and Stewart, R., *Colchicine induced tetraploids in carnations and poinsettias*, American Society for Horticultural Science 57: 408-410 (1951)).

However, the degree of difficulty and chance of successfully developing tetraploid plants varies with the genotype and method of application. For example in Pickens, K. A. and Cheng, M., *Effects of Colchicine and Oryzalin on Callus and Adventitious Shoot Formation of Euphorbia pulcherrima 'Winter Rose'* HortScience 41(7): 1651-1655 (2006), the authors discuss the fact that no tetraploid plants were developed in their experiments. Bernuetz (2001) developed a low number of tetraploid poinsettia plants by treating poinsettia cuttings with roots in aqueous solutions of colchicine ranging from 0.1%-0.3%.

It can be appreciated by one skilled in the art that the detailed method by which polyploidising agents are applied and the individual genotypes treated will result in unexpected outcomes. Surprisingly the inventor discovered a simple yet highly efficient method of producing polyploid poinsettias across a range of genotypes.

The present invention provides a method of altering the chromosome number of a *Euphorbia pulcherrima* plant to develop a tetraploid plant, with a chromosome number of 2n=56 comprising the steps of: (a) cultivating the *Euphorbia pulcherrima* plant; (b) applying an anti-mitotic agent to the growing points of the plant; (c) forcing shoots to emerge from the treated growing points of the plant; (d) selecting putative tetraploid shoots thus developed from the plant; (e) assessing the chromosome complement of the tetraploid shoots through cytological karyotype analysis; (f) growing the tetraploid shoot into a plant; and (g) checking chromosomal stability. It can be appreciated by one skilled in the art that the induction of tetraploidy can result in plants with chromosome numbers higher or lower than the expected tetraploid number and such aneuploid plants are herein defined as aneu-tetraploid.

Development of Plants with Non-Functional Small Cyathia (Backcross Triploid Hybrids)

Post-production longevity is a key desirable attribute in ornamental plants. Hybrids of *E. pulcherrima* and *E. cornastra* produce progeny with lower post-production longevity compared to the best traditional poinsettia cultivars (Bernuetz, pg 243, (2001)) probably because their cyathia abscise reasonably quickly and the period of consumer satisfaction is shorter. Dulce Rosa is known for its large cyathia size and relatively poor post production longevity (Dole, J., Hammer, A. and Barrett, J. *National Poinsettia trials—New releases for* 2006, Greenhouse Product News, February pp 22-26 (2006)). Therefore, improving cyathia retention has been the focus of some published work. Bernuetz (2001) in preliminary studies (data not presented) mentioned non-PoiBI infected hybrid plants had a short post-harvest period and this attribute should be improved. When the plants were infected with PoiBI post-production performance improved slightly. He suggested that backcrossing the *E. pulcherrima*×*E. cornastra* $F_1$ (diploid) hybrids to *E. pulcherrima* (diploid) plants with superior post-production performance could improve post-production performance in the progeny, but did not detail how this could be performed, and implied that cyathia retention could be improved. Evidence of successful diploid backcrossing could not be found in the available literature and lack of such plants could be due to the low success rate of this type of crossing, the rare development of male fertile $F_1$ (*E. pulcherrima*×*E. cornastra*) progeny to use, or perhaps the progeny developed were not commercially viable.

Surprisingly, the inventor found that when diploid *E. pulcherrima* plants were crossed as female parents with tetraploid *E. pulcherrima*×*E. cornastra* $F_1$ hybrid plants, many of the progeny possessed cyathia greatly reduced in size, not actually improved cyathia retention. These cyathia were small and non-functional, thus they unexpectedly improved the post-production performance of the plants through virtue of their small size. If these small non-functional cyathia abscised, the saleable product appearance was not significantly affected.

In poinsettias post-production performance has been investigated by numerous authors, including Nell, T. A., Leonard, R. T., Barrett, J. E., *Production factors affect the postproduction performance of poinsettia—a review, Acta Horticulturae* 405: 132-137 (1995); Nell, T. A. and Leonard, R. T., *Protecting poinsettias from postproduction losses, Grower Talks* July, pp. 98-104 (1996); Embry, J. L., and Nothnagel, E. A., *Leaf Senescence of Postproduction Poinsettias in Low-light Stress*, American Society for Horticultural Science 119(5):1006-1013 (1994) and Lee, Y, Derbyshire, P. J., Knox, P and Anne Kathrine Hvoslef-Eide, A. K., *Sequential cell wall transformations in response to the induction of a pedicel abscission event in Euphorbia pulcherrima (poinsettia)*, The Plant Journal, 54,993-1003 (2008)).

The first sign of plant deterioration post-production for a poinsettia or *Euphorbia pulcherrima*×*Euphorbia cornastra* interspecific hybrid is usually the abscission of cyathia, and the bracts subtending these cyathia beyond where the primary cyathium is attached, followed by abscission of the oldest lower leaves moving progressively upward until reaching the bracts below the primary cyathium, followed lastly by abscission of the bracts below the primary cyathium.

The inventor surprisingly found using the method herein described that backcross triploid interspecific hybrid plants with non-functional small cyathia could be developed thereby virtually eliminating the first stage of post-production deterioration.

The small non-functional cyathia are less than approximately 3 mm in diameter when fully mature and if/when they abscise tend to dehydrate and shrivel to a very small size which is virtually unnoticeable to the consumer. The bracts subtending these cyathia surprisingly do not abscise.

Another unexpected key benefit of non-functional small cyathia is their very low susceptibility to infection with the fungus *Botrytis cinerea*. This common greenhouse fungus grows on the anthers and nectar gland of cyathia in poinsettias and *Euphorbia pulcherrima*×*Euphorbia cornastra* interspecific hybrids and infection often causes the cyathia to abort prematurely. Infection of the plant with the fungus often leads to bract abscission and rotting of the upper bract branches leading to crop losses and unsaleable plants. The small non-functional cyathia of the plants which are the subject of the present invention do not possess anthers. They also frequently have greatly reduced cyathial glands that do not produce nectar. Both of these characteristics thereby reduce the potential of *Botrytis cinerea* infection and crop losses.

The present invention unexpectedly resulted in production of hybrid triploid plants with non-functional small cyathia. The method of the present invention used diploid *Euphorbia pulcherrima* plants as the female parent in an interspecific cross with a male parent of the pedigree "tetraploid (*Euphorbia pulcherrima*×*Euphorbia cornastra*)" wherein said cross comprised the following steps: (a) collecting pollen from the second plant; (b) pollinating a cyathium on the first plant with this pollen; (c) isolating an embryo resulting from the pollination by embryo rescue; (d) culturing the embryo on nutrient agar medium; (e) obtaining a hybrid plantlet resulting from the growth of this embryo; and (f) transplanting plantlets to a greenhouse growing medium where they developed into mature triploid hybrid plants.

By using a tetraploid (*Euphorbia pulcherrima*×*Euphorbia cornastra*) plant as the male parent the hybrid progeny unexpectedly possessed non-functional small cyathia compared to using a diploid (*Euphorbia pulcherrima*×*Euphorbia cornastra*) plant as a male parent, which never led to development of progeny with non-functional small cyathia.

It is a further aspect of the present invention that the hybrid plant of the present invention is a triploid as defined herein with a chromosome number of 2n=42.

It is a further aspect of the present invention to propagate a triploid hybrid plant comprising the steps of: (a) obtaining a cutting of a hybrid plant produced from the cross of a diploid *Euphorbia pulcherrima* plant as a female parent and a plant of the pedigree "tetraploid (*Euphorbia pulcherrima*× *Euphorbia cornastra*)" as a male parent; and (b) cultivating this cutting to obtain a triploid hybrid plant.

It is a further aspect of the present invention to provide a method for producing a triploid hybrid plant further defined by applying a plant hormone composition to the cutting base to induce the formation of roots to produce a tetraploid hybrid plant.

It is a further aspect of the present invention that the triploid *Euphorbia pulcherrima*×*Euphorbia cornastra* hybrid plant of the present invention is infected with Poinsettia Branch Inducing Phytoplasma (PoiBi).

In addition to the exemplary aspects and embodiments described above, further aspects and embodiments will become apparent by study of the following examples.

Development of Plants with Red Bracts and Non-Functional Small Cyathia (Interspecific Backcross Tetraploid Hybrids)

The flower industry strives to develop new and different varieties of flowering plants. An effective way to create such novel varieties is through the manipulation of flower color. Flower color is predominantly due to two types of pigments: flavonoids and carotenoids. Flavonoids contribute to a range of colors from yellow to red to blue. Carotenoids impart a reddish-orange or yellow tinge and are commonly the only pigment in yellow or orange flowers. The flavonoid molecules which make the major contribution to flower color are the anthocyanins, which are glycosylated derivatives of cyanidin, delphinidin, petunidin, peonidin, malvidin, and pelargonidin, and are localized in the vacuole. The different anthocyanins can produce marked differences in color. Flower color is also influenced by co-pigmentation with colorless flavonoids, metal complexation, glycosylation, acylation, methylation, and vacuolar pH. See, Forkman, G. *Flavonoids as flower pigments: the formation of the natural spectrum and its extension by genetic engineering*, Plant Breeding 106:1-26 (1991).

The present invention unexpectedly resulted in production of interspecific backcross tetraploid plants with red bract colour and the additional attribute of non-functional small cyathia. The red bract colour of the interspecific backcross tetraploid plants produced by the present invention is defined as including, but not limited to, the colours RHS N34A, N34B, 42A, 42B, 42C, 42D, 43A, 43B, 43C, 44A, 44B, 44C, 44D, 45A, 45B, 45C, 45D, 46A, 46B, 46C, 46D, 47A, 47B, 47C, 47D, 50A, 53A, 53B, 53C, 53D based on the Royal Horticultural Society Colour Chart, 2001. It can be appreciated by one skilled in the art that the interpretation of bract colour can vary due to a number factors, including growing temperatures, light intensity, nutrient application, chemical treatment for pests and diseases, soil water content, etc.

The method of the present invention used tetraploid *Euphorbia pulcherrima* plants as the female parent in an interspecific cross with a male parent of the pedigree "tetraploid (*Euphorbia pulcherrima*×*Euphorbia cornastra*)" wherein said cross comprised the following steps: (a) collecting pollen from the second plant; (b) pollinating a cyathium on the first plant with this pollen; (c) isolating an embryo resulting from the pollination by embryo rescue; (d) culturing the embryo on nutrient agar medium; (e) obtaining a plantlet resulting from the growth of this embryo; and (f) transplanting plantlets to a greenhouse growing medium where they developed into mature tetraploid plants.

It is a further aspect of the present invention that the hybrid plant of the present invention is a tetraploid as defined herein with a chromosome number of 2n=56.

It is a further aspect of the present invention to propagate a tetraploid hybrid plant comprising the steps of: (a) obtaining a cutting of a plant produced from the cross of a tetraploid *Euphorbia pulcherrima* plant as a female parent and a plant of the pedigree "tetraploid (*Euphorbia pulcherrima*×*Euphorbia cornastra*)" as a male parent; and (b) cultivating this cutting to obtain a tetraploid hybrid plant.

It is a further aspect of the present invention to provide a method for producing a tetraploid hybrid plant further defined by applying a plant hormone composition to the cutting base to induce the formation of roots to produce a tetraploid hybrid plant.

It is a further aspect of the present invention that the tetraploid *Euphorbia pulcherrima*×*Euphorbia cornastra* plant of the present invention is infected with Poinsettia Branch Inducing Phytoplasma (PoiBI).

In addition to the exemplary aspects and embodiments described above, further aspects and embodiments will become apparent by study of the following examples.

The genetics of bract colour inheritance in *E. pulcherrima* is reasonably simple, Stewart (1960) explained a single completely dominant gene designated WH is responsible for red bract colour. The homozygous whwh conferred white bract colour. Modifying factors exist, as there are a range of red and white bracted plants produced. Later, Stewart and Arisumi (1966) demonstrated that a second independent locus, termed pk was responsible for genetic pink bract colour in poinsettias when in the homozygous recessive form and having the genotype WH-- at the WH locus. The genotype pkpk reduced the amount of anthocyanin pigment formed when WH/-- (red) was established. Currently, in the Poinsettia market, pink cultivars appear to be all chimeric, and not genetically pink.

The author discovered unexpectedly when a poinsettia of genetic constitution WHWH, WHwh or whwh is crossed as a female parent with *E. cornastra* as a male parent the progeny are always a shade of pink. White and red were never produced from over 1,000 plants developed from numerous cross combinations during >10 years of breeding.

The author subsequently attempted treating several selected *Euphorbia pulcherrima*×*Euphorbia cornastra* cultivars with gamma radiation to induce mutations, with the aim of inducing a red bracted mutant. Surprisingly, red bracted mutants were never recorded from thousands of mutants observed over several years.

Backcrossing is another breeding method whereby the hybrid between *E. pulcherrima* and *E. cornastra* is used as a male parent in a cross to the original female parent (*E. pulcherrima*). Because most progeny from the *E. pulcherrima*×*E. cornastra* cross are male sterile, this route is difficult. The author attempted this method with a few rare male fertile *E. pulcherrima*×*E. cornastra* hybrid plants but none of the progeny exhibited red bracts.

Another option to develop a red bracted interspecific hybrid *E. pulcherrima*×*E. cornastra* plant might be to utilise the *E. pulcherrima*×*E. cornastra* hybrid as a female parent in further crossing. However, from over 1,000 seedlings produced none possessed female structures (style, stigma, ovary), they were completely female sterile. $F_1$ hybrids developed by crossing *E. pulcherrima* and *E. cornastra* have never been described in the literature with female fertility. In the current world market no cultivars of *E. pulcherrima*×*E. cornastra* have functional female appendages (stigma, style, ovary). On the rare occasion when a hybrid has been developed possessing some anthers, pollen viability is usually very low. Kobayashi (2001) reported pollen viability from 3-18% in $F_1$ hybrids developed in her program. This limits their use to male parents only.

Thus, prior to the present invention, the development of a red bracted *E. pulcherrima*×*E. cornastra* interspecific hybrid was not possible to obtain by methods obvious to one skilled in the art.

Infection with Poinsettia Branch Inducing Phytoplasma (PoiBI)

In one embodiment, a free-branching agent may be transmitted to a plant of the present invention by grafting a plant having a free branching agent with a plant of the present invention. The graft used may be any graft which results in transmission of the free-branching agent from the free-branching plant to a plant of the present invention. Preferably, the grafting method used to transmit the agent is an approach grafting method. An approach grafting method involves cutting a section of stem, preferably approximately 10 to 30 mm long and sufficiently deep to reach the cambium, in both the plant of the present invention and the free-branching plant, and subsequently maintaining the cut portions in contact with each other until transfer of the free-branching agent from the free-branching plant to the plant of the present invention has occurred. Cuttings may then be planted and plants having free-branching characteristics grown from the cuttings. In another embodiment, the free-branching agent may be transmitted to a plant of the present invention using a parasitic plant dodder (e.g. *Cuscuta* sp.). For example, the parasitic dodder may be used to transfer the free-branching agent from a free-branching plant to a non-free-branching plant. Suitably, the parasitic dodder may have the free-branching agent. The use of parasitic dodders for transmitting agents are known in the art and are described in, for example, Lee, I-M., Klopmeyer, M., Bartoszyk, I., Gunderson-Rindal, D., Chou, T., Thomson, K. and Eisenreich, R., Phytoplasma induced free-branching in commercial poinsettia cultivars, Nature Biotechnology 15: 178-182 (1997). In yet another embodiment, the free branching agent may be transmitted through a leaf hopper. Use of leaf hoppers for transmission of agents between plants in known, and described in, for example, McCoy, R., Caudwell, A., Chang, C., Chen, T., Chiykowski, L, Cousin, M., Dale, J., de Leeuw, G., Golino, D., Hackett, K., Kirkpatrick, B., Marwitz, R., Petzold, H., Sinha, R., Sugiura, M., Whitcomb, R., Yang, I., Zhu, B., Seemuller, E., Plant diseases associated with mycoplasma-like organisms, In: *The Mycoplasmas* 5: 545-563 (1989).

Poinsettia Branch-Inducing Phytoplasma (PoiBI) is often found in combination with viruses such as poinsettia mosaic virus (PnMV) and/or poinsettia cryptic virus (PnCV). Poinsettia plants carrying one or more of these agents include, for example, cv. V10 Amy red. However, it will be appreciated by those skilled in the art that the free-branching agent may be transferred to practically any *Euphorbia pulcherrima* or *Euphorbia pulcherrima*×*Euphorbia cornastra* hybrid of choice and that infected *Euphorbia* of choice may then be used to transmit the free-branching agent to a plant of the present invention. Confirmation that the free-branching agent has been transmitted to the *Euphorbia* of choice or a plant of the present invention may be achieved by techniques known in the art such as, for example, morphological examination to note the free-branching characteristics of the plant. In addition or alternatively, the actual free-branching agent may be detected using well known techniques such as PCR (polymerase chain reaction) or ISEM (immunosorbent electron microscopy).

Examples of free-branching *Euphorbia* plants that are suitable for use in the method include, for example, the *Euphorbia pulcherrima* varieties Freedom (U.S. Plant Pat. No. PP7,825), Success Red (U.S. Plant Pat. No. PP8,773), Red Velvet (U.S. Plant Pat. No. PP11,124), Peterstar (U.S. Plant Pat. No. PP8,259), Annette Hegg Dark Red (U.S. Plant Pat. No. PP3,160), and V-14 Glory (U.S. Plant Pat. No. PP4,384). The PRINCETTIA varieties described in the following plant patents (U.S. Plant Patents PP23,296; PP21,327; PP21,326; PP21,325; PP21324) can also be used.

EXAMPLES

The following examples are provided to further illustrate the present invention. These examples are not to be construed as limiting the scope of the invention in any manner beyond the limitations set forth in the appended claims. Many variations and modifications may be made while remaining within the spirit and the scope of the invention.

Example 1. Development of Tetraploid (*Euphorbia pulcherrima*×*Euphorbia cornastra*) Hybrid Plants for Use as Male Parents The present invention provides a new method for altering the chromosome number of a *Euphorbia pulcherrima*×*Euphorbia cornastra* plant to double the somatic chromosome number from diploid to tetraploid. Tetraploid *Euphorbia pulcherrima*×*Euphorbia cornastra* plants have not been previously reported in the available prior art. The method for altering the chromosome number of the present invention began with first cultivating a *Euphorbia pulcherrima*×*Euphorbia cornastra* plant and then an anti-mitotic agent, such as colchicine, trifluralin, oryzalin, or amiprophos-methyl (APM), was applied to the growing points of the *Euphorbia pulcherrima*×*Euphorbia cornastra* plant. Tetraploid shoots were then forced to emerge from the treated growing points of the *Euphorbia pulcherrima*×*Euphorbia cornastra* plant and the putative tetraploid shoots that had been developed from the growing points of the *Euphorbia pulcherrima*×*Euphorbia cornastra* plant were selected. The chromosome complement of the tetraploid shoots was then accessed through cytological karyotype analysis and the analyzed tetraploid shoots were then grown into a plant. Chromosomal stability of the new *Euphorbia pulcherrima*×*Euphorbia cornastra* plant was checked and the new tetraploid (*Euphorbia pulcherrima*×*Euphorbia cornastra*) plant was selected and maintained.

One aspect of the present invention involved the steps of obtaining a plant of the pedigree *Euphorbia pulcherrima*×*Euphorbia cornastra* with appropriate genetic characteristics useful for breeding for target traits, including, but not limited to, dark pink bracts, the production of an occasional anther containing some fertile pollen, reasonable post production performance, resistance to branch breakage, dark green foliage and compact habit. After the *Euphorbia pulcherrima*×*Euphorbia cornastra* plant was obtained, a tetraploid (*Euphorbia pulcherrima*×*Euphorbia cornastra*) plant was developed using the following method: cuttings were collected from vegetatively growing stockplants and the cut bases were dipped in 2000 ppm Indole-butyric acid powder and then planted into OASIS brand propagation wedges. The cuttings were then placed under intermittent mist in a propagation house maintained at approximately 20° C. After three weeks, the cuttings were acclimatized to greenhouse conditions and then each plant was potted into a 15 cm diameter pot filled with a standard nursery potting mix. The potted plants were placed in a greenhouse at 18° C. minimum temperature and long day photoperiod to prevent flowering. After about three weeks the plants were ready for colchicine application. One day before colchicine application the apical meristem was removed from each plant. Colchicine was prepared as a paste from 0.1%-3.0% weight/volume with a water soluble gel. A range of colchicine concentrations was used for treating the plants so that it could be determined which concentration gave optimal results for each line treated. The paste was liberally applied to the buds with a small brush and washed off using a fine water mist after 24 hours. The number of plants and buds painted was counted during application so that a measure of efficiency of production could be made upon completion.

For the next few weeks, plants were observed and maintained according to best practice and growth procedures (as described in: Ecke, P., Faust, J., Williams, J. and Higgins, A. *The Ecke Poinsettia Manual*, Ball Publishing (2004)). New shoots were assessed for signs of tetraploidy. These signs included: shoots with larger than normal foliage and wider petiole diameter. Following vegetative growth, the plants were allowed to flower under a short photoperiod of 10 hours. After approximately 7-9 weeks the flowering plants were observed and signs of tetraploidy were noted compared to controls for the following characteristics which indicated tetraploidy: larger cyathia, cyathia with fertile anthers, wider, longer and thicker bracts and leaves, and larger pollen diameter. Flowering shoots that appeared tetraploid were labeled, collected and propagated as described previously for vegetative cuttings.

Once fresh putative tetraploid shoots were produced, cuttings were taken and propagated. These second generation plants were continually assessed for stability and uniformity of tetraploidy based on phenotype. Putative tetraploids were then confirmed or discarded by performing karyotype analysis. After confirmation, plants were propagated at least two more times to ensure they were stable tetraploids. On a regular basis, the plants were visually examined for morphological characteristics of tetraploidy. Chromosome counts were performed on selected tetraploid lines of *Euphorbia pulcherrima×Euphorbia cornastra* developed.

The tetraploid (*Euphorbia pulcherrima×Euphorbia cornastra*) plants developed frequently possessed male fertility; however, they always lacked female fertility because the gynoecium was absent or greatly reduced and non-functional. This was a surprising result, because male fertility was improved but female fertility was not.

Table 1 shows the *Euphorbia pulcherrima×Euphorbia cornastra* plants treated with colchicine in column 1, the reason for selection in column 2, the treatment method in column 3, the number of selections made in column 4, and the number of plants kept and chromosome number of those plants in column 5. Table 1 also shows two plants produced by other methods—spontaneously and via gamma radiation treatment.

to double the somatic chromosome number from diploid to tetraploid. The method for altering the chromosome number of the present invention began with first cultivating a *Euphorbia pulcherrima* plant and then an anti-mitotic agent, such as colchicine, trifluralin, oryzalin, or amiprophosmethyl (APM), was applied to the growing points of the *Euphorbia pulcherrima* plant. Tetraploid shoots were then forced to emerge from the treated growing points of the *Euphorbia pulcherrima* plant and the putative tetraploid shoots that had been developed from the growing points of the *Euphorbia pulcherrima* plant were selected. The chromosome complement of the tetraploid shoots was then accessed through cytological karyotype analysis and the analyzed tetraploid shoots were then grown into a plant. Chromosomal stability of the new *Euphorbia pulcherrima* plant was checked and the new tetraploid *Euphorbia pulcherrima* plant was selected and maintained.

One aspect of the present invention involved the steps of obtaining a plant of *Euphorbia pulcherrima* with appropriate genetic characteristics useful for breeding for target traits, including, but not limited to, dark red bracts, male and female fertility, good post production performance, resistance to branch breakage, dark green foliage and compact habit. After the *Euphorbia pulcherrima* plant was obtained, a tetraploid *Euphorbia pulcherrima* plant was developed using the following method: cuttings were collected from vegetatively growing stockplants and the cut bases were dipped in 2000 ppm Indole-butyric acid powder and then planted into OASIS brand propagation wedges. The cuttings were then placed under intermittent mist in a propagation house maintained at approximately 20° C. After three weeks, the cuttings were acclimatized to greenhouse conditions and then each plant was potted into a 15 cm diameter pot filled with a standard nursery potting mix. The potted plants were placed in a greenhouse at 18° C. minimum temperature and long day photoperiod to prevent flowering. After about three weeks the plants were ready for colchicine application. One day before colchicine application the apical meristem was removed from each plant. Colchicine was prepared as a paste from 0.1%-3.0% weight/volume with a water soluble gel. A range of colchicine concentrations was used for

TABLE 1

| Diploid 2n = 28 (*E. pulcherrima* × *E. cornastra*) accession | Reason for selection | Treatment | Number of selections made | Accession number of tetraploid 2n = 56 plants kept |
|---|---|---|---|---|
| 9EC-1 | vigorous, partial male fertile | colchicine 1-3%, 12-24 hrs | 2 | 66, 76 |
| 127 | vigorous, partial male fertile | Gamma radiation Spontaneous mutation | 1 1 | 302, 880 |
| 187 | hot pink, overall good performance | colchicine 1-3%, 12-24 hrs | 3/168 buds treated | 457, 458, 459 |
| 240 | vigorous, partial male fertile | colchicine 1% bud application 24 hrs | >20/160 buds treated | 1111-1120 |
| 418 | deep pink, overall good performance | colchicine 1-3% bud application 24 hrs | 25/275 buds treated | 698, 703, 707, 708, 715 |
| 425 | light pink, overall good performance | colchicine 1-3% bud application 24 hrs | 44/350 buds treated | 722, 733, 744, 752, 755, 760 |
| 574 | deep pink, overall good performance | colchicine 1-3% bud application 24 hrs | 37/350 buds treated | 786, 788, 796, 798 |
| 614 | white with pink vein, overall good performance | colchicine 1-3% bud application 24 hrs | 49/225 buds treated | 810, 814, 816, 825, 837, 841, 847 |

Example 2. Development of Tetraploid *Euphorbia pulcherrima* Plants for Use as Female Parents The present invention provides a new method for altering the chromosome number of a *Euphorbia pulcherrima* plant treating the plants so that it could be determined which concentration gave optimal results for each line treated. The paste was liberally applied to the buds with a small brush and washed off using a fine water mist after 24 hours. The number of plants and buds painted was counted during application so that a measure of efficiency of production could be made upon completion.

For the next few weeks, plants were observed and maintained according to best practice and growth procedures (e.g., Ecke, et at (2004)). New shoots were assessed for signs of tetraploidy. These signs included: shoots with larger than normal foliage and wider petiole diameter. Following vegetative growth, the plants were allowed to flower under a short photoperiod of 10 hours. After approximately 7-9 weeks the flowering plants were observed and signs of tetraploidy were noted compared to controls for the following characteristics: larger cyathia, cyathia with fertile anthers, wider, longer and thicker bracts and leaves, and anthers with larger pollen diameter. Flowering shoots that appeared tetraploid were labeled, collected and propagated as described previously for vegetative cuttings.

Once fresh putative tetraploid shoots were produced, cuttings were taken and propagated. These second generation plants were continually assessed for stability and uniformity of tetraploidy based on phenotype. Putative tetraploids were then confirmed or discarded by performing karyotype analysis. After confirmation, plants were propagated at least two more times to ensure stability. On a regular basis, the plants were visually examined for morphological characteristics of tetraploidy. Chromosome counts were performed on selected tetraploid lines of *Euphorbia pulcherrima* developed. Table 2 shows the diploid *Euphorbia pulcherrima* plants treated with colchicine in column 1, the reason for selection in column 2, the treatment method in column 3, the number of selections made in column 4, and the number of plants kept and chromosome number of those plants in column 5.

(*Euphorbia pulcherrima*×*Euphorbia cornastra*)" plant being used as a male parent. Pollen was applied using a small brush onto a stigma of the diploid *Euphorbia pulcherrima* female plant when the *Euphorbia pulcherrima* stigma was receptive. Emasculation of the *Euphorbia pulcherrima* cyathia was not required as the parents used were outbreeding and do not self pollinate. After several weeks, successful crosses were noted by ovary swelling greater than unpollinated controls. The swollen ovaries were harvested either at 4 weeks post pollination, or just prior to abscission. From this point onward the embryo rescue method of Bernuetz (2006) was utilized to produce triploid (*Euphorbia pulcherrima*×*Euphorbia cornastra*) hybrid plants infected with PoiBI.

The method is included here for clarity. Aseptic technique was applied to each ovary. Ovaries were preferably placed intact into a vessel with 4% sodium hypochlorite added to cover the material, followed by one drop of Tween 20 detergent. The vessel was closed with a lid and shaken once per minute for five minutes. The vessel was then emptied and the ovaries rinsed three times in distilled autoclaved water. Ovaries were then removed and individually dissected. Each of the three locules was opened using a sterile scalpel and any developing ovules were removed. The embryo was then longitudinally bisected into two pieces and placed onto appropriate embryo rescue media in a 50 mL plastic screw top tube. The media preferably contained Murashige and Skoog (1962) salts (Murashige, T. and Skoog, F, *A revised medium for rapid growth and bio assays with tobacco tissue cultures*, Physiologia Plantarum, 15:473-497 (1962)), 1 g/l activated charcoal, 1 g/l casein hydrolysate, 4% sucrose and 7 g/l agar. Media was adjusted to pH

TABLE 2

| Diploid *Euphorbia pulcherrima* accession | Reason for selection | Colchicine treatment | Number of selections made | Accession number of tetraploid 2n = 56 plants kept |
|---|---|---|---|---|
| 26 | red bracts, good overall performance | 0.1-0.3%, 5 or 7 hrs | 7/116 un-rooted cuttings treated | 57, 58 |
| 32 | white bracts, good overall performance | 1-3%, 12-24 hrs | 7/~170 buds treated | 441, 442, 443, 444, |
| 49 | orange/red bracts, overall good performance | 0.1-0.3%, 5 or 7 hrs | 2/120 un-rooted cuttings treated | 55, 56, 59, 60 |
| 113 | bright red bracts, early flowering, overall good performance | 1-3%, 12-24 hrs | 8/~170 buds treated | 445, 446, 447, 448, 547 |
| 148 | lemon bracts, overall good performance | 1-3%, 12-24 hrs | 5/~170 buds treated | 454, 457 |
| 149 | burgundy bracts, reasonable overall performance | 1-3%, 12-24 hrs | 5/~170 buds treated | 439.1 |
| 151 | red bracts, overall good performance | 1-3%, 12-24 hrs | 7/~170 buds treated | 449, 451.1, 452, 452.2, 551, 552 |
| 152 | dark burgundy small bracts, reasonable overall performance | 1-3%, 12-24 hrs | 11/~170 buds treated | 553, 554, 557 |

Example 3. Method of Hybridisation to Produce Backcross Triploid (*Euphorbia pulcherrima*×*Euphorbia cornastra*) Hybrid Plants with Small Non-Functional Cyathia Another aspect of the present invention involved crossing a diploid plant of *Euphorbia pulcherrima* with a plant of the pedigree "tetraploid (*Euphorbia pulcherrima*×*Euphorbia cornastra*)". The diploid *Euphorbia pulcherrima* plants were selected for appropriate characteristics to use in breeding for desired target traits, such as, dark red bracts, male and female fertility, good post production performance, resistance to branch breakage, dark green foliage and compact habit. Pollen was then removed from a selected "tetraploid 5.8 prior to autoclaving at 1 kg/m$^2$ at 121° C. for seventeen minutes. Tubes containing dissected embryos were placed into a growth chamber at 25° C.+/−2° C. under white fluorescent lights to provide a light intensity of approximately 60-70 μmol m$^{-2}$s$^{-1}$ at culture container lid level for 16 hrs/day. Developing embryos were subcultured onto the above mentioned regeneration media or a proliferation media containing MS basal salts, 0.3 mg/l 6-benzyl amino purine, 1 g/l casein hydrolysate, 40 g/L sucrose and 7 g/L agar with a pH adjusted to 5.8 prior to autoclaving. Subsequent subculturing was performed at approximately 3 to 4 week intervals onto fresh media of either composition depending upon growth.

Plantlets (primary plants) developed in vitro were deflasked by either planting the regenerated plantlets emerged directly from embryos or by cutting and dipping developed shoots in 2000 mg/L IBA powder, prior to placement in expanded OASIS propagation wedges. A constant water mist was initially applied and later gradually reduced to facilitate acclimatisation once plantlets had developed roots. Plants were grown under standard practices as described in Ecke et al (2004).

To produce a commercially viable plant with high branching, the Poinsettia Branch Inducing Phytoplasma (PoiBI) was introduced. Vegetative cuttings were harvested from the new triploid (*E. pulcherrima*×*E. cornastra*) plants and approach grafted to a poinsettia cultivar infected with PoiBI. Approach grafting involved cutting a vertical section of the stem on both plants of approximately 20 to 30 mm in length and deep enough to cut through to the cambium, then the two cut portions were placed facing each other and the graft union sealed with parafilm M laboratory film. The cuttings were then propagated under a water mist, followed by hardening-off and production in a pot following standard production practices for poinsettias. Upon development of sufficient growth (e.g. 10 weeks), PoiBI infected cuttings were removed from the grafted triploid (*E. pulcherrima*×*E. cornastra*) plant and these cuttings were then used to establish PoiBI infected stock of the cultivar.

Example 4. Method of Hybridisation to Produce Backcross Tetraploid (*Euphorbia pulcherrima*×*Euphorbia cornastra*) Plants with Small Non-Functional Cyathia and Red Bracts Another aspect of the present invention involved crossing a tetraploid plant of *Euphorbia pulcherrima* with a plant of the pedigree "tetraploid (*Euphorbia pulcherrima*×*Euphorbia* cornastra)". The tetraploid *Euphorbia pulcherrima* plants were selected for appropriate characteristics to use in breeding for desired target traits, such as, dark pink bracts, the production of an occasional anther containing some fertile pollen, reasonable post production performance, resistance to branch breakage, dark green foliage and compact habit. Pollen was then removed from a selected "tetraploid (*Euphorbia pulcherrima*×*Euphorbia cornastra*)" plant being used as a male parent. Pollen was applied using a small brush onto a stigma of the tetraploid *Euphorbia pulcherrima* female plant when the stigma was receptive. Emasculation of the *Euphorbia pulcherrima* cyathia was not required as the parents used were outbreeding and do not self pollinate. After several weeks, successful crosses were noted by ovary swelling greater than unpollinated controls. The swollen ovaries were harvested either at 4 weeks post pollination, or just prior to abscission. From this point onward the embryo rescue method of Bernuetz (2006) was utilized to produce new tetraploid (*Euphorbia pulcherrima*× *Euphorbia* cornastra) hybrid plants infected with PoiBI (as outlined previously in Example 3).

Example 5. Description of Crossing Performed and Results Obtained

Crossing was performed as described in examples 3 and 4. Results of crossing are tabulated in Tables 3, 4 and 5 below. Table 3 shows the results of cross pollinations conducted using diploid *Euphorbia pulcherrima* as a female parent and tetraploid (*Euphorbia pulcherrima*×*Euphorbia cornastra*) as a male parent to produce triploid progeny with small cyathia (<3 mm in diameter). Table 3, column 1 shows the female parent (diploid *Euphorbia pulcherrima*), column 2 shows the male parent tetraploid (*Euphorbia pulcherrima*× *Euphorbia pulcherrima*), column 3 shows the number of triploid plants produced with cyathia less than 3 mm in diameter, column 4 shows the number of triploid plants produced with cyathia greater than 3 mm in diameter and column 5 shows the bract colour of the triploid plants produced. In Table 3, for the bract colour, all triploid plants developed were pink and various shades were observed but not categorized.

TABLE 3

| Female Parent (diploid *Euphorbia pulcherrima*) | Male Parent tetraploid (*Euphorbia pulcherrima* × *Euphorbia cornastra*) | Triploid plants with <3 mm cyathia diameter | Triploid plants with >3 mm cyathia diameter | Bract colour of triploid plants |
|---|---|---|---|---|
| 24 | 66 | 2 | 0 | Pink |
| 24 | 76 | 20 | 4 | Pink |
| 32 | 76 | 1 | 0 | Pink |
| 49 | 66 | 1 | 0 | Pink |
| 49 | 76 | 0 | 1 | Pink |
| 49 | 457 | 2 | 0 | Pink/orangey tinge |
| 49 | 722 | 3 | 0 | Pink |
| 49 | 744 | 0 | 1 | Pink |
| 49 | 825 | 2 | 1 | Pink |
| 49 | 837 | 1 | 3 | Pink |
| 49 | 841 | 0 | 1 | Pink |
| 53 | 837 | 0 | 1 | Pink |
| 53 | 847 | 1 | 0 | Pink |
| 81 | 457 | 4 | 1 | Pink |
| 81 | 755 | 1 | 0 | Pink |
| 81 | 825 | 1 | 0 | Pink |
| 81 | 841 | 1 | 0 | Pink |
| 81 | 847 | 1 | 0 | Pink |
| 83 | 457 | 0 | 1 | Pink |
| 83 | 810 | 1 | 0 | Pink |
| 106 | 66 | 1 | 0 | Pink |
| 113 | 457 | 2 | 0 | Pink |
| 113 | 722 | 1 | 0 | Pink |
| 113 | 744 | 0 | 2 | Pink |
| 113 | 755 | 1 | 2 | Pink |
| 148 | 847 | 0 | 1 | Pink |
| 150 | 457 | 1 | 1 | Pink |
| 150 | 744 | 0 | 1 | Pink |
| 150 | 841 | 0 | 1 | Pink |
| 150 | 847 | 0 | 1 | Pink |
| 151 | 810 | 1 | 1 | Pink |
| 151 | 814 | 0 | 1 | Pink |
| 352 | 76 | 1 | 1 | Pink |
| 356 | 66 | 0 | 1 | Pink |
| 362 | 66 | 0 | 1 | Pink |
| 365 | 76 | 3 | 2 | Pink |
| 366 | 66 | 7 | 0 | Pink |
| 366 | 302 | 3 | 0 | Pink |
| 367 | 66 | 1 | 0 | Pink |
| 367 | 76 | 1 | 0 | Pink |
| 377 | 76 | 0 | 3 | Pink |
| 378 | 76 | 1 | 1 | Pink |
| 379 | 76 | 1 | 0 | Pink |
| 392 | 302 | 2 | 0 | Pink |
| 392 | 457 | 1 | 0 | Pink |
| 392 | 814 | 1 | 0 | Pink |
| 392 | 1112 | 2 | 0 | Pink |
| 395 | 66 | 2 | 0 | Pink |
| 406 | 76 | 1 | 0 | Pink |
| 411 | 66 | 2 | 1 | Pink |
| 478 | 457 | 0 | 2 | Pink |
| 478 | 744 | 0 | 1 | Pink |
| 478 | 816 | 1 | 0 | Pink |
| 478 | 825 | 0 | 1 | Pink |
| 478 | 847 | 3 | 0 | Pink |
| 853 | 457 | 2 | 1 | Pink |
| 04-360 | 302 | 1 | 1 | Pink |
| Total | 57 cross combinations | 85 | 41 | All Pink |

As shown in Table 3, 57 different cross combinations were performed and the percentage of triploid progeny with small cyathia less than 3 mm in diameter from this crossing work was 85/126=67.5%. 100% of the triploid progeny had pink bracts. Crosses using rare diploid *Euphorbia pulcherrima*× *Euphorbia cornastra* male parent plants that possessed some male fertility were also performed using diploid *Euphorbia pulcherrima* plants as female parents. Table 4 presents the results of this crossing. It is very difficult to obtain male fertile diploid (*Euphorbia pulcherrima*×*Euphorbia cornastra*) plants to perform the crossing because they are rarely produced using the method of Bernuetz (2006) and Kobayashi (2000). In Table 4 three diploid *Euphorbia pulcherrima*×*Euphorbia cornastra* male parent plants that possessed some male fertility were used in 15 different combinations with diploid *Euphorbia pulcherrima* female parents.

Table 4 shows the results of cross pollinations conducted using diploid *Euphorbia pulcherrima* as a female parent and diploid (*Euphorbia pulcherrima*×*Euphorbia cornastra*) as a male parent. Table 4, column 1 shows the female parent (diploid *Euphorbia pulcherrima*), column 2 shows the male parent diploid (*Euphorbia pulcherrima*×*Euphorbia cornastra*), column 3 shows the number of diploid plants produced with cyathia less than 3 mm in diameter, column 4 shows the number of diploid plants produced with cyathia greater than 3 mm in diameter, and column 5 shows the bract colour of the diploid plants produced. In Table 4, where noted, some diploid plants produced a proportion of cyathia which were less than 3 mm in diameter, but also other branches where cyathia were greater than 3 mm in diameter, and these were noted as unstable.

TABLE 4

| Female Parent (diploid *Euphorbia pulcherrima*) | Male Parent tetraploid (*Euphorbia pulcherrima* × *Euphorbia cornastra*) | Diploid plants with <3 mm cyathia diameter | Diploid plants with >3 mm cyathia diameter | Bract colour of diploid plants |
|---|---|---|---|---|
| 27 | 221 | 0 | 2 | Pink (very unstable) |
| 31 | 221 | 0 | 1 | Pink (very unstable) |
| 49 | 214 | 0 | 2 | Pink |
| 83 | 221 | 0 | 3 | Pink |
| 351 | 221 | 0 | 1 | Pink |
| 362 | 221 | 0 | 4 | Pink |
| 365 | 209 | 0 | 1 | Pink (unstable) |
| 366 | 221 | 0 | 3 | Pink |
| 367 | 221 | 0 | 2 | Pink |
| 370 | 209 | 0 | 1 | Pink |
| 374 | 221 | 0 | 1 | Pink |
| 377 | 221 | 0 | 2 | Pink |
| 400 | 209 | 0 | 3 | Pink |
| 04-360 | 221 | 0 | 1 | Pink (unstable) |
| Total | 15 cross combinations | 0 | 27 | All Pink |

As shown in Table 4, none of the diploid plants had cyathia consistently less than 3 mm in diameter and 100% had pink bracts. The results from Table 3 and Table 4 demonstrate that the method of the present invention is superior in efficiency (67.5% vs. 0%) for developing *Euphorbia pulcherrima*×*Euphorbia cornastra* plants with small cyathia. Both methods developed 100% of plants with pink bracts. It was noted that plants in Table 4 with greater than 3 mm cyathia in diameter often had highly variable cyathia diameters and the cyathia were not often uniform within the same bract cluster, which is an undesirable commercial attribute.

When crossing is performed at the tetraploid level, i.e. tetraploid *Euphorbia pulcherrima* as a female parent and tetraploid (*Euphorbia pulcherrima*×*Euphorbia cornastra*) as a male parent, not only does the proportion of plants with small cyathia increase, but the added benefit of red bracts is observed in all the tetraploid progeny developed. Table 5 shows the results of cross pollinations conducted using tetraploid *Euphorbia pulcherrima* as a female parent and tetraploid (*Euphorbia pulcherrima*×*Euphorbia cornastra*) as a male parent to produce tetraploid progeny with small non-functional cyathia and red bracts. Table 5, column 1 shows the female parent (tetraploid *Euphorbia pulcherrima*), column 2 shows the male parent tetraploid (*Euphorbia pulcherrima*×*Euphorbia cornastra*), column 3 shows the number of tetraploid plants produced with cyathia less than 3 mm in diameter, column 4 shows the number of tetraploid plants produced with cyathia greater than 3 mm in diameter and column 5 shows the bract colour of the tetraploid plants produced.

TABLE 5

| Female Parent (diploid *Euphorbia pulcherrima*) | Male Parent tetraploid (*Euphorbia pulcherrima* × *Euphorbia cornastra*) | Tetraploid plants with <3 mm cyathia diameter | Tetraploid plants with >3 mm cyathia diameter | Bract colour of tetraploid plants |
|---|---|---|---|---|
| 55 | 76 | 2 | 0 | Red |
| 55 | 707 | 1 | 0 | Red |
| 55 | 715 | 1 | 0 | Red |
| 55 | 788 | 1 | 0 | Red |
| 55 | 796 | 2 | 0 | Red |
| 55 | 798 | 1 | 0 | Red |
| 59 | 76 | 13 | 0 | Red |
| 445 | 4 × 187 mixed pollen | 2 | 0 | Red |
| 445 | 457 | 3 | 0 | Red |
| 445 | 459 | 2 | 0 | Red |
| 445 | 707 | 1 | 0 | Red |
| 445 | 715 | 1 | 0 | Red |
| 445 | 796 | 2 | 0 | Red |
| 446 | 703 | 3 | 0 | Red |
| 446 | 798 | 2 | 0 | Red |
| 447 | 457 | 19 | 1 | Red |
| 447 | 703 | 5 | 0 | Red |
| 447 | 715 | 1 | 0 | Red |
| 447 | 796 | 1 | 0 | Red |
| 447 | 798 | 1 | 0 | Red |
| 447 | 810 | 4 | 0 | Red |
| 448 | 457 | 3 | 0 | Red |
| 448 | 703 | 3 | 0 | Red |
| 448 | 707 | 1 | 0 | Red |
| 448 | 796 | 3 | 0 | Red |
| 448 | 810 | 6 | 1 | Red |
| 449 | 457 | 2 | 0 | Red |
| 451.1 | 810 | 1 | 0 | Red |
| 452 | 457 | 3 | 0 | Red |
| 452 | 459 | 1 | 0 | Red |
| 452 | 810 | 1 | 0 | Red |
| 452.2 | 457 | 1 | 0 | Red |
| 454 | 457 | 2 | 0 | Red |
| 454 | 716 | 1 | 0 | Red |
| 454 | 810 | 2 | 0 | Red |

TABLE 5-continued

| Female Parent (diploid Euphorbia pulcherrima) | Male Parent tetraploid (Euphorbia pulcherrima × Euphorbia cornastra) | Tetraploid plants with <3 mm cyathia diameter | Tetraploid plants with >3 mm cyathia diameter | Bract colour of tetraploid plants |
|---|---|---|---|---|
| 546 | 796 | 1 | 0 | Red |
| 547 | 457 | 2 | 0 | Red |
| 547 | 703 | 5 | 0 | Red |
| 547 | 707 | 5 | 0 | Red |
| 547 | 715 | 5 | 0 | Red |
| 547 | 788 | 1 | 0 | Red |
| 547 | 796 | 4 | 0 | Red |
| 547 | 798 | 3 | 0 | Red |
| 551 | 457 | 5 | 1 | Red |
| 551 | 1116 | 1 | 0 | Orange/Red |
| 552 | 457 | 1 | 0 | Red |
| Total | 46 cross combinations | 131 | 3 | All red |

As shown in Table 5, 46 different cross combinations were performed and the percentage of tetraploid progeny with small cyathia less than 3 mm in diameter from this crossing work was 97.8%. 100% of the tetraploid progeny had red bracts. The small percentage of plants (2.2%) that had medium or large cyathia was attributed to rare diploid pollen or other unusual effects of the unique cytological environment of the polyploid interspecific hybrids, possibly causing non-tetraploid plants to develop, most likely aneu-tetraploid. Selected plants were grafted to a PoiBI infected *Euphorbia* to introduce PoiBI. After several months PoiBI infected plants were selected to be grown in a comparative trial and measurements were taken at the end of the trial to determine the cyathia diameter, bract colour and chromosome numbers, results are shown in Table 6. Plants were propagated at the same time from 7 week old vegetative shoots collected from stockplants grown under natural long day conditions in a greenhouse. After propagation the plants were planted into 15 cm pots filled with a conventional potting mix suitable for the growth of poinsettias. The plants were allowed to grow for 3 weeks and were then pinched by removing the top 1-2 cm of apical growth. Plants were drip irrigated and fertilised according to standard nursery practices for growing poinsettias (see: Ecke et. al. (2004)). After 2 weeks the plants were subjected to a natural short photoperiod sufficiently short to allow flower initiation and development. After 10 weeks from the start of short photoperiod all plants were fully developed and measurements were taken. The RHS (Royal Horticultural Society, 2001) Colour charts were utilised for determining the young and mature bract colour of each plant. Measurements were taken from three young bracts on three plants per accession. Measurements were also taken of three mature bracts on three plants per accession. Cyathia diameter was measured with vernier calipers by measuring the widest section of three cyathia (either 1$^{st}$ or second order) on three plants from each accession, and then deriving an average. Chromosome numbers were assessed by cytological preparations of root tips. Plant height, width and number of branches was also recorded, but data is not presented.

Table 6 shows the phenotypic and chromosomal characterisation of selected plants developed as a result of the new invention, their parents and commercially available cultivars. Table 6, column 1 shows the accession number, column 2 shows the type of plant, column 3 shows the pedigree, column 4 shows the observed chromosome number, column 5 shows the young bract RHS colour measured on the young bracts of three plants, column 6 shows the young bract colour description, column 7 shows mature bract RHS colour measured on the mature bracts of three plants, column 8 shows the mature bract colour description and column 9 shows the average cyathia diameter of the largest three cyathia measured on three replicate plants of each accession (average of 9 measurements). Chromosome numbers marked with a superscript "1" were cytologically verified and photographs taken.

TABLE 6

| Accession number | Type of plant | Pedigree | Chromosome number | Young bract colour (RHS) | Young bract colour description | Mature bract colour (RHS) | Mature bract colour description | Average mature cyathia diameter (mm) |
|---|---|---|---|---|---|---|---|---|
| 16 | *Euphorbia cornastra* | *Euphorbia cornastra* seedling | 2n = 28 | 155C | White | 155C | White | 4.2 |
| 113 | *Euphorbia pulcherrima* | *Euphorbia pulcherrima* cultivar | 2n = 28 | Near 46B, darker than mature bracts | Bright red | Near 46B | Bright red | 6.9 |
| 128 | *E. pulcherrima* × *E. cornastra* | "Dulce Rosa" cultivar | 2n = 28[1] | N57A | Pink | N57C | Pink | 8.5 |
| 151 | *Euphorbia pulcherrima* | *Euphorbia pulcherrima* cultivar | 2n = 28 | Near 46B, darker than mature bracts | Deep red | Near 46B | Deep red | 6.6 |
| 187 | *E. pulcherrima* × *E. cornastra* | PRINCETTIA cultivar | 2n = 28 | N57B | Pink | N57C | Pink | 5.5 |
| 241 | *E. pulcherrima* × *E. cornastra* | Non-commercialised PRINCETTIA type | 2n = 28[1] | N57B | Dark pink | N57B | Dark pink | 6.9 |
| 276 | *E. pulcherrima* × *E. cornastra* | PRINCETTIA cultivar | 2n = 28 | 155A | White with pink vein | 155B | White with pink vein | 6.1 |
| 418 | *E. pulcherrima* × *E. cornastra* | PRINCETTIA cultivar | 2n = 28[1] | N57A | Dark pink | N57B | Dark pink | 6.1 |
| 445 | Tetraploid *E. pulcherrima* | tetraploid form of 113 | 2n = 56[1] | 46A | Red | 46B | Red | 8.1 |

TABLE 6-continued

| Accession number | Type of plant | Pedigree | Chromosome number | Young bract colour (RHS) | Young bract colour description | Mature bract colour (RHS) | Mature bract colour description | Average mature cyathia diameter (mm) |
|---|---|---|---|---|---|---|---|---|
| 447 | Tetraploid *E. pulcherrima* | tetraploid form of 113 | 2n = 56 | 46A | Red | 46B | Red | 8.1 |
| 448 | Tetraploid *E. pulcherrima* | tetraploid form of 113 | 2n = 56 | 46A | Red | 46B | Red | 8.0 |
| 452 | Tetraploid *E. pulcherrima* | tetraploid form of 151 | 2n = 56[1] | 46A | Red | 46A | Red | 8.3 |
| 457 | Tetraploid (*E. pulcherrima* × *E. cornastra*) | tetraploid form of 187 | 2n = 56[1] | N57D | Pink | N57C | Pink | 8.4 |
| 515 | Triploid backcross | *E. pulcherrima* 392 × tetraploid (*E. pulcherrima* × *E. cornastra*) 302 | 2n = 42[1] | N57A | Cherry pink | N57B | Cherry pink | 1.7 |
| 703 | Tetraploid (*E. pulcherrima* × *E. cornastra*) | tetraploid form of 418 | 2n = 56[1] | N57A | Dark pink | N57B | Dark pink | 7.2 |
| 796 | Tetraploid (*E. pulcherrima* × *E. cornastra*) | tetraploid mutant form of 187 | 2n = 56[1] | N57A | Dark pink | N57B | Dark pink | 7.5 |
| 814 | Tetraploid (*E. pulcherrima* × *E. cornastra*) | tetraploid mutant form of 187 | 2n = 56 | 155B with pink vein | Pale pink | 65B | Pink | 7.3 |
| 906 | Tetraploid backcross | *E. pulcherrima* 447 × 457 | 2n = 56 | 53A | Red | 53C, more reddish | Red | 1.5 |
| 907 | Tetraploid backcross | *E. pulcherrima* 447 × 457 | 2n = 56 | 53A | Red | 53C, more reddish | Red | 1.5 |
| 936 | Tetraploid backcross | *E. pulcherrima* 445 × 457 | 2n = 56 | 53A | Red | 53C, more reddish | Red | 1.9 |
| 937 | Tetraploid backcross | *E. pulcherrima* 447 × 457 | 2n = 56 | 53A | Red | 53C, more reddish | Red | 1.9 |
| 938 | Tetraploid backcross | *E. pulcherrima* 447 × 457 | 2n = 56 | 53A | Red | 53C, more reddish | Red | 1.9 |
| 939 | Tetraploid backcross | *E. pulcherrima* 447 × 457 | 2n = 56 | 53A | Red | N57B | Dark Pink | 1.9 |
| 941 | Tetraploid backcross | *E. pulcherrima* 551 × 457 | 2n = 56 | 53A | Red | N57B | Dark Pink | 1.9 |
| 958 | Tetraploid backcross | *E. pulcherrima* 551 × 457 | 2n = 56 | 53A | Red | N57B | Dark Pink | 1.7 |
| 959 | Tetraploid backcross | *E. pulcherrima* 551 × 457 | 2n = 56 | 53A | Red | N57B | Dark Pink | 1.9 |
| 960 | Tetraploid backcross | *E. pulcherrima* 447 × 457 | 2n = 56 | 53A | Red | 53A, darker reddish | Red | 1.1 |
| 961 | Tetraploid backcross | *E. pulcherrima* 447 × 457 | 2n = 56 | 53A | Red | N57B | Dark Pink | 1.1 |
| 962 | Tetraploid backcross | *E. pulcherrima* 445 × 457 | 2n = 56 | 53A | Red | N57B | Dark Pink | 1.3 |
| 1092 | Triploid backcross | *E. pulcherrima* 83 × 457 | 2n = 42[1] | 58B | Dark cherry pink | 58B | Dark cherry pink | 5.2 (highly variable) |
| 1093 | Tetraploid backcross | *E. pulcherrima* 448 × 457 | 2n = 56[1] | 46A or 53A | Red | 53C but more red | Red | 1.4 |
| 1095 | Triploid backcross | *E. pulcherrima* 151 × 810 | 2n = 42 | N57A | Cherry pink | N57A | Cherry pink | 6.7 |
| 1096 | Triploid backcross | *E. pulcherrima* 151 × 814 | 2n = 42[1] | 58B | Dark cherry pink | 58B | Dark cherry pink | 7.3 |
| 1097 | Tetraploid backcross | *E. pulcherrima* 447 × 810 | 2n = 56 | 46A or 53A | Red | 53C but more red | Red | 1.9 |
| 1099 | Tetraploid backcross | *E. pulcherrima* 448 × 810 | 2n = 56 | 46A or 53A | Red | 53C but more red | Red | 1.6 |
| 1100 | Tetraploid backcross | *E. pulcherrima* 448 × 810 | 2n = 56 | 46A or 53A | Red | 53C but more red | Red | 1.4 |
| 1101 | Tetraploid backcross | *E. pulcherrima* 448 × 810 | 2n = 56[1] | 53A | Red | 53C but more red | Red | 1.7 |
| 1109 | Tetraploid backcross | *E. pulcherrima* 448 × 810 | 2n = 56 | 58B but more red | Red | 58B | Dark Cherry Pink | 2.2 |

Because interspecific hybrid backcross seedlings are devoid of PoiBI they need to be grafted to introduce this phytoplasma for commercial production. To determine if PoiBI significantly influenced cyathia diameter or bract colour, three accessions were included in the previously mentioned trial with and without PoiBi infection. The results are shown in Table 7. Table 7, column 1 shows the accession number, column 2 shows PoiBI infection status (+=infected, −=not infected), column 3 shows the type of plant, column 4 shows the pedigree, column 5 shows the chromosome number, column 6 shows the young bract RHS colour measured on the young bracts of three plants, column 7 shows the young bract colour description, column 8 shows mature bract RHS colour measured on the mature bracts of three plants, column 9 shows the mature bract colour description and column 10 shows the average mature cyathia diameter of the largest three cyathia measured on three replicate plants of each accession (average of 9 measurements).

TABLE 7

| Accession number | PoiBI | Type of plant | Pedigree | Chromosome number | Young bract colour (RHS) | Young bract colour description | Mature bract colour (RHS) | Mature bract colour description | Average mature cyathia diameter (mm) |
|---|---|---|---|---|---|---|---|---|---|
| 113 | − | Euphorbia pulcherrima | Euphorbia pulcherrima cultivar | 2n = 28 | Near 46B, darker than mature bracts | Bright red | Near 46B | Bright red | 6.8 |
| 113 | + | Euphorbia pulcherrima | Euphorbia pulcherrima cultivar | 2n = 28 | Near 46B, darker than mature bracts | Bright red | Near 46B | Bright red | 6.9 |
| 151 | − | Euphorbia pulcherrima | Euphorbia pulcherrima cultivar | 2n = 28 | Near 46B, darker than mature bracts | Deep red | Near 46B | Deep red | 6.7 |
| 151 | + | Euphorbia pulcherrima | Euphorbia pulcherrima cultivar | 2n = 28 | Near 46B, darker than mature bracts | Deep red | Near 46B | Deep red | 6.6 |
| 187 | − | E. pulcherrima × E. cornastra | PRINCETTIA cultivar | 2n = 28 | N57B | Pink | N57C | Pink | 5.2 |
| 187 | + | E. pulcherrima × E. cornastra | PRINCETTIA cultivar | 2n = 28 | N57B | Pink | N57C | Pink | 5.5 |

As shown in Table 7, PoiBI infection did not significantly influence cyathia diameter.

Numerous other breeding cross combinations including various ploidies of both male and female parents were performed to try and develop novel Euphorbia pulcherrima×Euphorbia cornastra hybrid plants. Table 8 shows the results of the cross combinations attempted and the theoretical parental genetic contributions to offspring according to cross type and a description of the plants developed. Table 8, column 1 shows the female parent, column 2 shows the gamete chromosome contribution of the female parent, column 3 shows the male parent, column 4 shows the gamete chromosome contribution of the male parent, column 5 shows the somatic (2n) chromosome number, column 6 shows the percent contribution of Euphorbia pulcherrima, column 7 shows the percent contribution of Euphorbia cornastra, column 8 shows the progeny description and column 9 shows notes.

TABLE 8

| Female parent | Gamete chromosome contribution | Male parent | Gamete chromosome contribution | Somatic (2n) chromosome number | % contribution of E. pulcherrima | % contribution of E. cornastra | Progeny description | Note |
|---|---|---|---|---|---|---|---|---|
| E. pulcherrima | n = 14 | E. cornastra | n = 14 | 2n = 28 | 50% | 50% | Always pink bracts, medium to large cyathia | Standard method of Kobayashi (2000) and Bernuetz (2006) |
| Tetraploid E. pulcherrima | n = 28 | E. cornastra | n = 14 | 2n = 42 | 67% | 33% | Pink bracts, mainly large cyathia | Cyathia often unstable |
| E. pulcherrima | n = 14 | Tetraploid E. cornastra | n = 28 | 2n = 42 | 33% | 66% | Pink bracts, large fuzzy cyathia, poor growth | Cyathia unstable |
| Tetraploid E. pulcherrima | n = 28 | Tetraploid E. cornastra | n = 28 | 2n = 56 | 50% | 50% | Pink bracts, mainly large cyathia | |
| E. pulcherrima | n = 14 | E. pulcherrima × E. cornastra | n = 7 n = 7 | 2n = 28 | 75% | 25% | Pink bracts, mainly large cyathia | Male fertile plants are rare for male parent |
| E. pulcherrima | n = 14 | Tetraploid (E. pulcherrima × E. cornastra) | n = 14 n = 14 | 2n = 42 | 67% | 33% | Pink to hot pink bracts, high proportion with small non-functional cyathia | |
| Tetraploid E. pulcherrima | n = 28 | Tetraploid (E. pulcherrima × E. cornastra) | n = 14 n = 14 | 2n = 56 | 75% | 25% | Red bracts, small non-functional cyathia | Only combination with red bract plants and small non-functional cyathia |
| Tetraploid E. pulcherrima | n = 28 | E. pulcherrima × E. cornastra | n = 7 n = 7 | 2n = 42 | 83% | 17% | Pink to hot pink bracts, small to large cyathia | Male fertile male parents are rare to obtain |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A triploid (2n=42) or tetraploid (2n=56) interspecific hybrid *Euphorbia* plant or plant part thereof produced from a cross between a *Euphorbia pulcherrima* plant as a female parent and a male parent plant which is an interspecific hybrid of *Euphorbia pulcherrima*×*Euphorbia cornastra*, wherein the female parent plant is diploid (2n=28) or tetraploid (2n=56) and the male parent plant is tetraploid (2n=56).

2. The plant part of claim 1, wherein said plant part is selected from the group consisting of protoplasts, leaves, stems, roots, root tips, anthers, pistils, seed, embryo, pollen, ovules, cotyledon, hypocotyl, cyathium, bract, shoot, tissue, petiole, cells, and meristematic cells.

3. An interspecific hybrid plant or plant part thereof clonally propagated from the plant of claim 1.

4. The interspecific hybrid plant of claim 1, wherein said plant has non-functional small cyathia.

5. The interspecific hybrid plant of claim 1, wherein said plant has red bracts.

6. A method of producing an interspecific hybrid plant comprising:
   (a) crossing a *Euphorbia pulcherrima* plant as a female parent with a plant of *Euphorbia pulcherrima*×*Euphorbia cornastra* as a male parent, wherein the female parent plant is diploid (2n=28) or tetraploid (2n=56) and the male parent plant is tetraploid (2n=56);
   (b) producing an embryo from said cross; and
   (c) growing said embryo to obtain an interspecific backcross hybrid plant.

7. The method of claim 6, further comprising the steps of:
   (a) producing first and second plants, wherein the first plant is the male tetraploid plant of *Euphorbia pulcherrima*×*Euphorbia cornastra* and the second plant is the diploid or tetraploid *Euphorbia pulcherrima* female plant;
   (b) collecting pollen from said first plant;
   (c) pollinating a flower on said second plant with said pollen;
   (d) isolating an embryo resulting from said pollination by embryo rescue in tissue culture; and
   (e) growing said embryo to obtain an interspecific hybrid backcross plant.

8. An interspecific backcross hybrid plant or part thereof produced by the method of claim 6.

9. An interspecific backcross hybrid plant or part thereof produced by the method of claim 7.

10. A method of producing an interspecific backcross hybrid plant comprising the steps of:
    (a) obtaining a cutting of an interspecific backcross hybrid plant produced from the cross of a *Euphorbia pulcherrima* plant as a female parent and a plant of *Euphorbia pulcherrima*×*Euphorbia cornastra* as a male parent, wherein the female parent plant is diploid (2n=28) or tetraploid (2n=56) and the male parent plant is tetraploid (2n=56); and
    (b) growing said cutting to obtain an intergeneric hybrid plant.

11. An interspecific backcross hybrid plant produced by the method of claim 10.

12. The triploid or tetraploid interspecific hybrid plant of claim 1 possessing the Poinsettia Branch Inducing Phytoplasma (PoiBI).

* * * * *